US00PP30405P2

(12) United States Plant Patent
Ten Have

(10) Patent No.: US PP30,405 P2
(45) Date of Patent: Apr. 16, 2019

(54) ***CAMPANULA* PLANT NAMED 'HAVPRTB709'**

(50) Latin Name: *Campanula portenschlagiana*
Varietal Denomination: HAVPRTB709

(71) Applicant: Theodorus C. L. Ten Have, Honselersduk (NL)

(72) Inventor: Theodorus C. L. Ten Have, Honselersduk (NL)

(73) Assignee: Gebr. Ten Have B.V., Honselersdijk (NL)

( * ) Notice: Subject to any disclaimer, the term of this patent is extended or adjusted under 35 U.S.C. 154(b) by 0 days.

(21) Appl. No.: 15/732,572

(22) Filed: Nov. 29, 2017

(51) Int. Cl.
*A01H 5/02* (2018.01)

(52) U.S. Cl.
USPC ..... Plt./414

(58) Field of Classification Search
USPC ..... Plt./414
CPC ..... A01H 5/02; A01H 5/00; A01H 6/264
See application file for complete search history.

*Primary Examiner* — June Hwu
(74) *Attorney, Agent, or Firm* — C. A. Whealy

(57) ABSTRACT

A new and distinct cultivar of *Campanula* plant named 'HAVPRTB709' characterized by its compact, upright to outwardly spreading plant habit; freely branching habit; early and freely flowering habit; campanulate-shaped flowers with bright violet-colored petals; and good container and garden performance.

2 Drawing Sheets

Botanical designation: *Campanula portenschlagiana.*
Cultivar denomination: 'HAVPRTB709'.

BACKGROUND OF THE INVENTION

The present invention relates to a new and distinct cultivar of *Campanula* plant, botanically known as *Campanula portenschlagiana*, commonly known as Dalmatian Bellflower and hereinafter referred to by the name 'HAVPRTB709'.

The new *Campanula* is a product of a planned breeding program conducted by the Inventor in Honselersdijk, The Netherlands. The objective of the breeding program is to create new compact and freely flowering *Campanula* plants with attractive flowers and resistance to *Botrytis.*

The new *Campanula* plant originated from a cross-pollination conducted by the Inventor in Honselersdijk, The Netherlands on Jul. 16, 2014 of *Campanula portenschlagiana* 'Porto', not patented, as the female, or seed, parent with a proprietary selection of *Campanula portenschlagiana* identified as code number 1403, not patented, as the male, or pollen, parent. The new *Campanula* plant was discovered and selected by the Inventor as a single flowering plant from within the progeny of the stated cross-pollination grown in a controlled environment greenhouse in Honselersdijk, The Netherlands on May 19, 2015.

Asexual reproduction of the new *Campanula* plant by terminal cuttings in Honselersdijk, The Netherlands, since Aug. 18, 2015 has shown that the unique features of this new *Campanula* plant are stable and reproduced true to type in successive generations.

SUMMARY OF THE INVENTION

Plants of the new *Campanula* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HAVPRTB709'. These characteristics in combination distinguish 'HAVPRTB709' as a new and distinct *Campanula* plant:

1. Compact, upright to outwardly spreading plant habit.
2. Freely branching habit.
3. Early and freely flowering habit.
4. Campanulate-shaped flowers with bright violet-colored petals.
5. Good container and garden performance.

Plants of the new *Campanula* differ from plants of the female parent, 'Porto', in the following characteristics:

1. Plants of the new *Campanula* are more compact than plants of 'Porto'.
2. Flower color of plants of the new *Campanula* is more intense in color than flower color of plants of 'Porto'.

Plants of the new *Campanula* differ from plants of the male parent selection in the following characteristics:

1. Plants of the new *Campanula* are more compact than plants of the male parent selection.
2. Plants of the new *Campanula* have larger flowers than plants of the male parent selection.

Plants of the new *Campanula* can be compared to plants of *Campanula portenschlagiana* 'Addenda Intense Blue', not patented. In side-by-side comparisons, plants of the new *Campanula* differ primarily from plants of 'Addenda Intense Blue' in the following characteristics:

1. Plants of the new *Campanula* have longer lateral branches than plants of 'Addenda Intense Blue'.
2. Plants of the new *Campanula* have larger flowers than plants of 'Addenda Intense Blue'.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the colors of the new *Campanula* plant.

The photograph on the first sheet is a side perspective view of a typical flowering plant of 'HAVPRTB709' grown in a container.

The photograph on the second sheet is a close-up view of a typical flowering plant of 'HAVPRTB709'.

DETAILED BOTANICAL DESCRIPTION

Plants used for the aforementioned photographs and following description were grown during the winter and early spring in 11-cm containers in a glass-covered greenhouse in Honselersdijk, The Netherlands and under cultural practices typical of commercial *Campanula* plant production conditions. During the production of the plants, day temperatures ranged from 17° C. to 18° C., night temperatures ranged from 16° C. to 17° C. and light levels averaged 2,000 lux. Plants were ten weeks old when the photographs and description were taken. In the following description, color references are made to The Royal Horticultural Society Colour Chart, 2015 Edition, except where general terms of ordinary dictionary significance are used.

Botanical classification: *Campanula portenschlagiana* 'HAVPRTB709'.

Parentage:

*Female, or seed, parent.*—*Campanula portenschlagiana* 'Porto', not patented.

*Male, or pollen, parent.*—Proprietary selection of *Campanula portenschlagiana* identified as code number 1403, not patented.

Propagation:

*Type.*—By terminal cuttings.

*Time to initiate roots, summer.*—About 25 days at temperatures about 20° C.

*Time to initiate roots, winter.*—About 25 days at temperatures about 21° C.

*Time to produce a rooted young plant, summer.*—About 45 days at temperatures about 23° C.

*Time to produce a rooted young plant, winter.*—About 50 days at temperatures about 21° C.

*Root description.*—Fine, fibrous; typically creamy white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Herbaceous perennial; compact, upright to outwardly spreading plant habit; flattened globular in shape; moderately vigorous growth habit; moderate growth rate.

*Plant height, soil level to top of foliar plane.*—About 9.4 cm.

*Plant height, soil level to top of floral plane.*—About 13.2 cm.

*Plant width.*—About 25.5 cm.

*Lateral branch description.*—Branching habit: Freely branching habit with about 35 primary branches each with about four secondary branches developing per plant. Aspect: Upright to prostrate, ranging from about 0° to 80° from vertical. Length: About 7.6 cm. Diameter: About 1.75 mm. Internode length: About 1.9 cm. Strength: Moderately strong. Texture and luster: Moderately pubescent; moderately glossy. Color, developing: Close to 144B. Color, developed: Close to 144A to 144B.

Leaf description:

*Arrangement.*—Alternate, simple.

*Length.*—About 1.9 cm.

*Width.*—About 2.5 cm.

*Shape.*—Reniform.

*Apex.*—Broadly and bluntly acute.

*Base.*—Reniform to broadly attenuate.

*Margin.*—Coarsely and irregularly dentate.

*Texture and luster, upper surface.*—Smooth, glabrous; slightly glossy.

*Texture and luster, lower surface.*—Smooth, glabrous; matte.

*Venation pattern.*—Pinnate.

*Color.*—Developing leaves, upper surface: Close to 143A. Developing leaves, lower surface: Close to 138A. Fully developed leaves, upper surface: Close to NN137A; venation, close to 143A. Fully developed leaves, lower surface: Close to 137B; venation, close to 146B.

*Petioles.*—Length: About 4.2 cm. Diameter: About 1 mm. Texture and luster, upper and lower surfaces: Smooth, glabrous; glossy. Color, upper surface: Close to 146C. Color, lower surface: Close to 144A.

Flower description:

*Flower arrangement and shape.*—Single campanulate flowers arranged in axillary and terminal cymes; flowers face upright to slightly outwardly; freely flowering habit with about nine flowers developing per inflorescence and about 1,250 flowers developing per plant during the flowering season.

*Natural flowering season.*—Early flowering habit; plants begin flowering about 70 days after planting; in the garden, flowering continuous from spring into the autumn in The Netherlands.

*Flower longevity on the plant.*—About ten days; flowers persistent.

*Fragrance.*—Faintly fragrant; sweet and pleasant.

*Inflorescence height.*—About 8.3 cm.

*Inflorescence diameter.*—About 7 cm.

*Flower buds.*—Length: About 1.4 cm. Diameter: About 4 mm. Shape: Narrowly oblong to oblanceolate. Texture and luster: Smooth, glabrous; glossy. Color: Close to 86A; ribs, close to 85C to 85D.

*Flower diameter.*—About 3.3 cm.

*Flower length (height).*—About 2.2 cm.

*Flower throat diameter.*—About 1.2 cm.

*Flower tube diameter, distally.*—About 1.3 cm.

*Flower tube length.*—About 1.5 cm.

*Petals.*—Quantity and arrangement: Five in a single whorl; lower 52% of petal length fused. Length: About 1.9 cm. Width, at the base of the free part of the petal: About 9 mm; at the petal lobe's broadest part, about 1 cm. Shape: Fused portion, oblanceolate; lobe, obovate. Apex: Bluntly acute to obtuse. Margin: Entire. Texture and luster, upper surface: Smooth, glabrous; slightly velvety; matte. Texture and luster, lower surface: Smooth, glabrous; slightly glossy. Color: When opening, upper surface: Close to between 83A and N87A; towards the base, close to N87B. When opening, lower surface: Close to N87B. Fully opened, upper surface: Close to N87A; venation, close to N87A; color does not fade with development. Fully opened, lower surface: Close to N87B; venation, close to N87B; color does not fade with development. Flower throat: Close to N87A; venation, close to N87A. Flower tube: Close to N87B; venation, close to N87B.

*Sepals*.—Quantity and arrangement: Five in a single campanulate whorl. Length: About 5.5 mm. Width: About 1 mm. Shape: Lanceolate. Apex: Acute. Base: Broadly cuneate. Margin: Entire. Texture and luster, upper surface: Smooth, glabrous; slightly glossy. Texture and luster, lower surface: Smooth, glabrous; moderately glossy. Color: When developing and fully developed, upper surface: Close to 137C. When developing and fully developed, lower surface: Close to 137D.

*Peduncles*.—Length: About 6.1 cm. Diameter: About 1 mm. Aspect: Terminal inflorescences, upright; axillary inflorescences, about 50° from stem axis. Strength: Moderately strong. Texture and luster: Moderately pubescent; slightly glossy. Color: Close to 144A to 144B.

*Pedicels*.—Length: About 2.3 cm. Diameter: About 8 mm. Aspect: Terminal flowers, upright; axillary flowers, about 50° from peduncle axis. Strength: Moderately strong. Texture and luster: Smooth, glabrous; moderately glossy. Color: Close to 144B.

*Reproductive organs*.—Stamens: Quantity per flower: Five. Filament length: About 1.5 mm. Filament color: Close to NN155D. Anther size: About 6 mm by 0.2 mm. Anther shape: Narrowly oblong. Anther color: Close to 4C. Pollen amount: Scarce to moderate. Pollen color: Close to 4D. Pistils: Quantity per flower: One. Pistil length: About 1.2 cm. Stigma diameter: About 4 mm. Stigma shape: Decurrent; three-parted. Stigma color: Close to 90B. Style length: About 1.1 cm. Style color: Close to N88D. Ovary color: Close to 144A.

*Seeds and fruits*.—Seed and fruit production have not been observed on plants of the new *Campanula* to date.

Disease & pest resistance: Plants of the new *Campanula* have not been observed to be resistant to pathogens and pests common to *Campanula* plants to date.

Garden performance: Plants of the new *Campanula* have exhibited good tolerance to rain, wind and temperatures ranging from about −35° C. to about 35° C. and to be suitable for USDA Hardiness Zones 3 to 9.

It is claimed:

1. A new and distinct *Campanula* plant named 'HAVPRTB709' as illustrated and described.

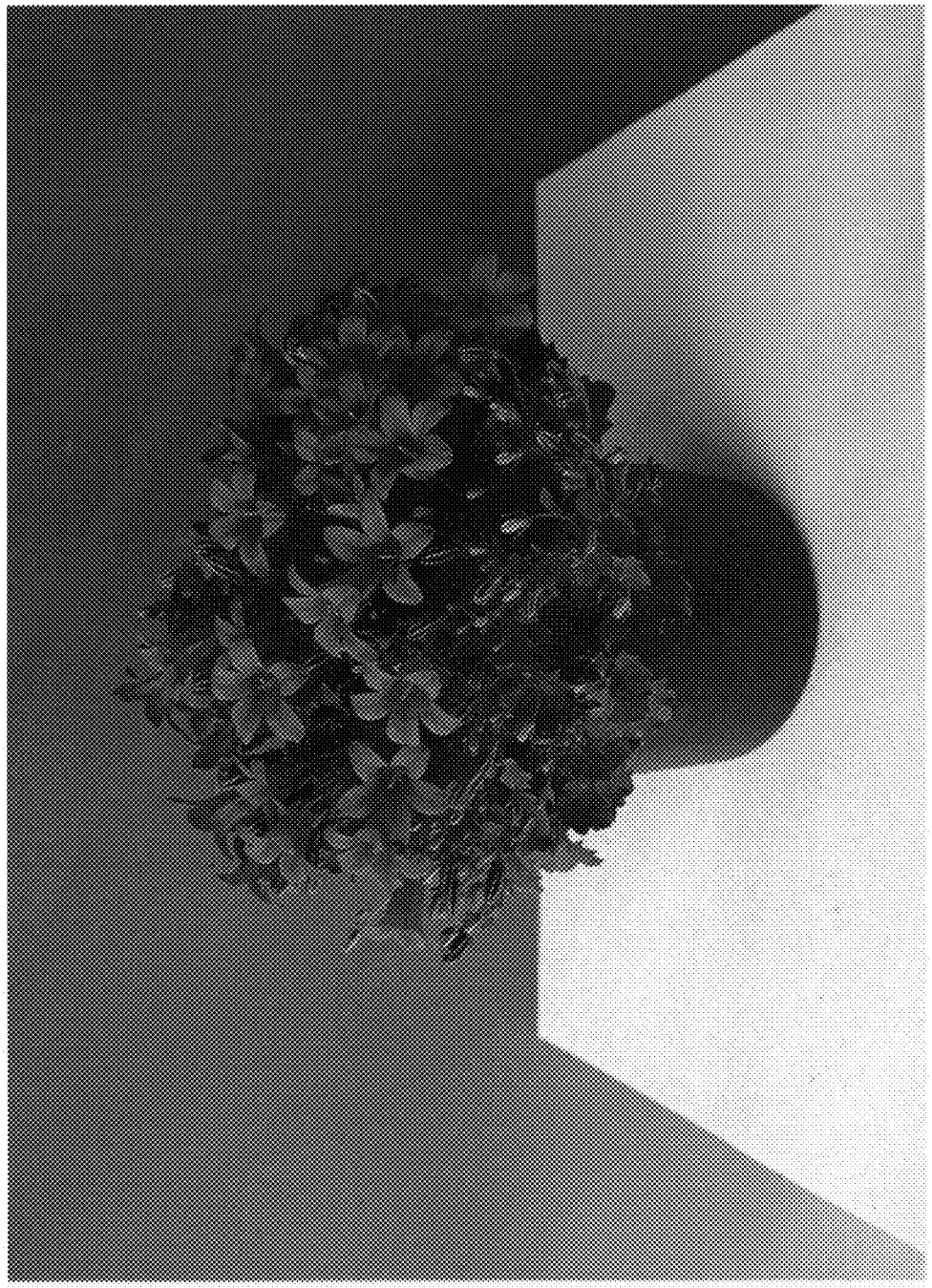

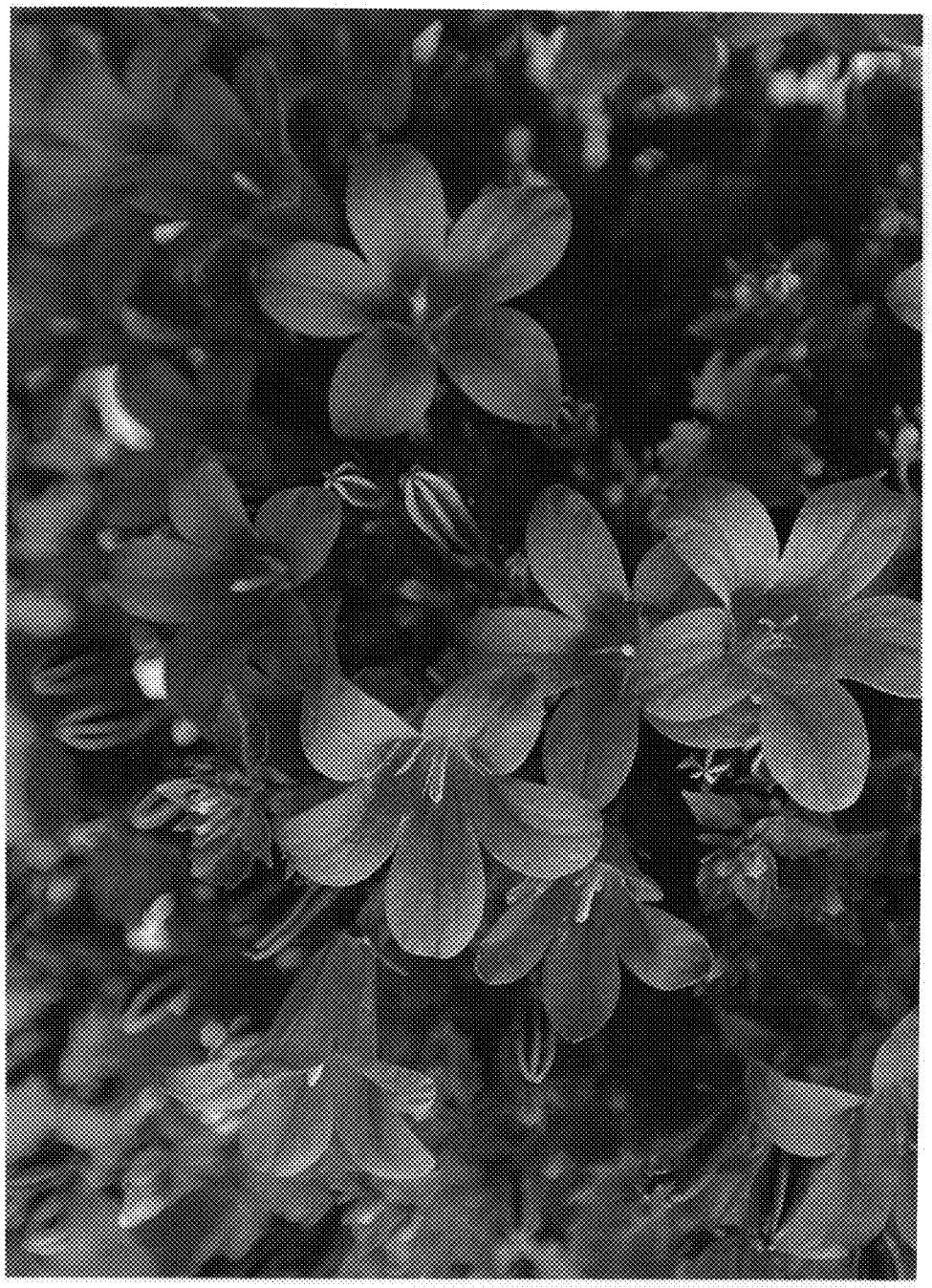

* * * * *